United States Patent [19]
Morford et al.

[11] Patent Number: 6,037,516
[45] Date of Patent: Mar. 14, 2000

[54] METHOD FOR REMOVAL OF OXYGENATE IMPURITIES FROM ORGANIC CHEMICAL STREAMS

[75] Inventors: Peter S. Morford; Timothy L. Lambert, both of Austin; William K. Culbreth, III, Beaumont, all of Tex.

[73] Assignee: Huntsman ICI Chemicals LLC, Austin, Tex.

[21] Appl. No.: 08/975,523

[22] Filed: Nov. 20, 1997

[51] Int. Cl.[7] ................................................ C07C 7/10
[52] U.S. Cl. ..................... 585/836; 585/856; 208/263; 208/273; 208/256; 208/259; 208/271; 208/283; 208/284; 208/286
[58] Field of Search ..................... 585/836, 856; 208/263, 273, 256, 259, 271, 283, 284, 286

[56] References Cited

U.S. PATENT DOCUMENTS

| | | | |
|---|---|---|---|
| 3,281,489 | 10/1966 | Goering | 585/251 |
| 3,535,399 | 10/1970 | Tabler | 585/854 |
| 3,816,478 | 6/1974 | Washall et al. | 260/348 R |
| 3,843,328 | 10/1974 | Bosanac | 23/270.5 |
| 3,881,996 | 5/1975 | Schmidt . | |
| 4,125,568 | 11/1978 | Theriot et al. | 585/834 |
| 4,296,263 | 10/1981 | Worrell . | |
| 4,547,598 | 10/1985 | Sanderson et al. . | |
| 4,691,034 | 9/1987 | Sanderson et al. | 549/542 |
| 4,691,035 | 9/1987 | Sanderson et al. | 549/542 |
| 4,704,482 | 11/1987 | Sanderson et al. . | |
| 4,705,903 | 11/1987 | Sanderson et al. . | |
| 4,742,179 | 5/1988 | Sanderson et al. . | |
| 4,873,380 | 10/1989 | Sanderson et al. . | |
| 4,910,349 | 3/1990 | Sanderson et al. . | |
| 4,912,266 | 3/1990 | Sanderson et al. . | |
| 4,912,267 | 3/1990 | Sanderson et al. . | |
| 4,922,033 | 5/1990 | Sanderson et al. . | |
| 4,922,034 | 5/1990 | Sanderson et al. . | |
| 4,933,499 | 6/1990 | Grotenhuis et al. | 568/438 |
| 5,000,825 | 3/1991 | Shih et al. . | |
| 5,059,730 | 10/1991 | Strebelle | 570/238 |
| 5,107,002 | 4/1992 | Shih | 549/542 |
| 5,157,205 | 10/1992 | Welton | 585/853 |
| 5,185,480 | 2/1993 | Sanderson et al. . | |
| 5,243,091 | 9/1993 | Kruse et al. . | |
| 5,292,964 | 3/1994 | Gupta . | |
| 5,354,912 | 10/1994 | Hwan et al. . | |
| 5,354,917 | 10/1994 | Sanderson et al. . | |
| 5,364,981 | 11/1994 | Knifton et al. . | |
| 5,386,065 | 1/1995 | Kruse et al. . | |
| 5,387,721 | 2/1995 | Kruse et al. . | |
| 5,395,982 | 3/1995 | Cassata et al. . | |
| 5,440,058 | 8/1995 | Hoffman et al. | 549/538 |
| 5,457,243 | 10/1995 | Knifton et al. . | |
| 5,616,814 | 4/1997 | Preston . | |
| 5,723,698 | 3/1998 | Dai et al. . | |

FOREIGN PATENT DOCUMENTS

| | | |
|---|---|---|
| 132 966 | 11/1978 | Germany . |
| 687991 | 2/1953 | United Kingdom . |

OTHER PUBLICATIONS

Bobylev et al., "A new method for the production of alcohols by catalytic cleavage," *J. organic Chem. Of the USSR*, 21(5, Part 2):1028–1029, 1985.

Ponec and Bond, *Catalysis by Metals and Alloys*, pp. 520–524; Elsevier: Amsterdam (1995).

Co–pending U. S. Patent Application Serial No. 08/727,718 filed Oct. 7, 1996.

Co–pending U. S. Patent Application Serial No. 08/966,879 filed Nov. 10, 1997, (HNSC:005).

Co–pending U. S. Patent Application Serial No. 09/253,687 filed Feb. 18, 1999, (HNSC:019).

International Search Report dated Feb. 26, 1999, (PCT/US98/24757)(Client ref. 81,455).

*Primary Examiner*—Walter D. Griffin
*Attorney, Agent, or Firm*—O'Keefe, Egan & Peterman

[57] ABSTRACT

Oxygenate impurities are removed from an organic chemical feed or stream by treatment with an aqueous reducing agent and aqueous base, accompanied by separation. An aqueous solution of reducing agent and an aqueous solution of base are typically introduced sequentially into the organic chemical stream, where they may react with any oxygenate impurities present. The reaction products of the oxygenate impurities and aqueous reducing agent and aqueous base are water soluble, and are typically removed in sequential fashion via any suitable separation means. For example, oxygenate impurities such as formaldehyde, acetaldehyde, propionaldehyde, and methyl formate may be removed from a propylene stream by treating the stream sequentially with aqueous sodium bisulfite and aqueous sodium hydroxide, accompanied by separation of the oxygenate impurity reaction products in coalescers.

33 Claims, 1 Drawing Sheet

METHOD FOR REMOVAL OF OXYGENATE IMPURITIES FROM ORGANIC CHEMICAL STREAMS

BACKGROUND OF THE INVENTION

1. Field of the Invention

The present invention relates generally to a process for removing impurities from feeds or streams comprising organic liquids. More particularly, it concerns the removal of aldehydes, esters, and related oxygenate impurities from feeds or streams comprising organic chemicals such as hydrocarbons and epoxides.

2. Description of Related Art

During the commercial manufacture of alkylene oxides, oxygenate impurities such as aldehydes and esters are typically produced. Such oxygenate impurities can be very difficult to separate from the alkylene oxide product, due to the small differences in boiling points and other physical properties between the product and the impurities. For example, in the manufacture of propylene oxide, a great deal of effort typically must be devoted to separating the product from the close boiling formaldehyde, acetaldehyde, methyl formate, and other impurities.

Numerous processes have been developed for separating alkylene oxide product from accompanying oxygenate impurities. For example, U.S. Pat. No. 4,691,034 discloses a process for removing methyl formate from propylene oxide via contacting the product mixture with an aqueous calcium hydroxide slurry to which a solubilizer has been added. Similarly, U.S. Pat. No. 4,691,035 discloses a process for removing methyl formate from propylene oxide via contacting the product mixture with a base such as sodium hydroxide in water and glycerol. A method for removal of methyl formate from ethylene oxide, propylene oxide, and butylene oxide by contacting the alkylene product mixture with a basic ion exchange resin is disclosed in U.S. Pat. No. 5,107,002. While these processes address the removal of methyl formate impurities which may be present in alkylene oxide product mixtures, they do not address the removal of aldehyde impurities which may also be present in alkylene oxide product mixtures.

U.S. Pat. No. 3,816,478 discloses a method for removal of aldehyde impurities from organic liquids by passing the organic liquids over a bed consisting essentially of solid particles of sodium bisulfite. However, this method does not address the removal of ester impurities, such as methyl formate, which may also be present in alkylene oxide streams.

SUMMARY OF THE INVENTION

In one broad respect, the present invention comprises a method for removing oxygenate impurities from an organic chemical feed or stream by means of introducing an aqueous solution of reducing agent and an aqueous solution of base into the organic chemical stream, where the reducing agent and base may react with any oxygenate impurities present. The reaction products of the oxygenate impurities and aqueous reducing agent and aqueous base are typically water soluble and, by virtue of this fact, may be removed from organic chemical streams via any convenient means of separation.

In one embodiment, this invention comprises a method for removing oxygenate impurities such as aldehydes and esters from a propylene feed or stream. In this method, aqueous sodium bisulfite (sodium hydrogen sulfite) is introduced into the propylene stream, and the propylene and aqueous bisulfite are mixed by passing through a static mixer, resulting in the formation of a first emulsion. This first emulsion is introduced into a first coalescer and contacted with a coalescing pad, which serves to separate the emulsion into a first propylene or organic layer and a first aqueous layer within the first coalescer. A first portion of the first aqueous layer is discarded or disposed, and a second portion of the first aqueous layer is recycled by reintroducing the second portion of the first aqueous layer into the propylene stream at a point near or coincident with the point at which aqueous sodium bisulfite is introduced into the propylene stream. The first propylene layer is removed from the first coalescer. Upon removal from the first coalescer, the first propylene layer typically comprises a first propylene effluent stream which may be at least partially free of oxygenate impurities. Aqueous sodium hydroxide is introduced into the first propylene effluent stream, and the propylene effluent stream and aqueous sodium hydroxide are mixed by passing through a static mixer, resulting in the formation of a second emulsion. This second emulsion is introduced into a second coalescer comprising a sand coalescing filter. The second emulsion contacts the sand coalescing filter, which serves to separate the emulsion into a second propylene or organic layer and a second aqueous layer within the second coalescer. A first portion of the second aqueous layer is discarded or disposed, and a second portion of the second aqueous layer is recycled by reintroducing the second portion of the second aqueous layer into the first propylene effluent stream at a point near or coincident with the point at which aqueous sodium hydroxide is introduced into the first propylene effluent stream. The second propylene layer is then removed from the second coalescer. Upon removal from the second coalescer, the second propylene layer comprises a second propylene effluent stream which may be substantially free of oxygenate impurities.

In one embodiment, this invention is a method for purifying an organic chemical stream comprising one or more oxygenate impurities An aqueous reducing agent is introduced into the organic chemical stream under conditions such that the aqueous reducing agent reacts with at least a first portion of the oxygenate impurities to form one or more aqueous phase reduction products or aqueous phase first reaction products. The aqueous phase first reaction products are removed from the organic chemical stream to form a first purified organic chemical stream.

In another embodiment of the invention, an aqueous base is introduced into the organic chemical stream comprising one or more oxygenate impurities under conditions such that the aqueous base reacts with at least a second portion of the oxygenate impurities to form one or more aqueous phase second reaction products. The aqueous phase second reaction products are removed from the organic chemical stream to form a second purified organic chemical stream.

In one embodiment of the invention, the organic chemical stream comprises at least one of an alkane, alkene, alkylene oxide or a mixture thereof, where the alkane comprises at least one of methane, ethane, propane, butane, isobutane, or a mixture thereof, the alkene comprises at least one of ethene, propene, 1-butene, 2-butene, or a mixture thereof, and the alkylene oxide comprises at least one of ethylene oxide, propylene oxide, butylene oxides, or a mixture thereof. The oxygenate impurities present in the organic chemical stream comprise at least one of an aldehyde, ester, carboxylic acid, or a mixture thereof, where aldehyde comprises at least one of formaldehyde, acetaldehyde, propionaldehyde, butyraldehyde, isobutyraldehyde, or a mixture thereof, the ester comprises at least one of methyl formate, ethyl formate, propyl formate, butyl formate, isobutyl formate, methyl acetate, ethyl acetate, propyl acetate, butyl acetate, isobutyl acetate, or a mixture thereof, and the carboxylic acid comprises at least one of formic acid, acetic acid, propionic acid, butyric acid, isobutyric acid, or a mixture thereof.

In one typical embodiment of the disclosed invention, a reducing agent comprises at least one of sulfurous acid, sodium bisulfite, sodium sulfite, sodium metabisulfite, or a mixture thereof, and a base comprises at least one of lithium hydroxide, sodium hydroxide, potassium hydroxide, cesium hydroxide, or a mixture thereof.

In another typical embodiment of the disclosed invention, the organic chemical stream comprises propylene and the oxygenate impurities therein comprise at least one of an aldehyde, ester, or a mixture thereof.

In one respect, the present invention is a method for purifying an organic chemical stream comprising one or more oxygenate impurities The method comprises several steps. In one step, an aqueous reducing agent is introduced into an organic chemical stream and the aqueous reducing agent and the organic chemical stream are mixed such that a first emulsion is formed and such that the aqueous reducing agent reacts with at least a first portion of the oxygenate impurities to form one or more aqueous phase first reaction products. In another step, the first emulsion is separated into a first organic chemical phase and a first aqueous phase comprising the aqueous phase first reaction products. In another step, the first aqueous phase is removed from the first organic chemical phase such that the first organic chemical phase comprises a first purified organic chemical stream. An aqueous base is introduced into the first purified organic chemical stream and the aqueous base and the first purified organic chemical stream are mixed such that a second emulsion is formed and such that the aqueous base reacts with the oxygenate impurities to form one or more aqueous phase second reaction products. In another step, the second emulsion is separated into a second organic chemical phase and a second aqueous phase comprising the aqueous phase second reaction products. Finally, the second aqueous phase is removed from the second organic chemical phase such that the second organic chemical phase comprises a second purified organic chemical stream.

An organic chemical stream treated by the method of the present invention typically comprises at least one of an alkane, alkylene, alkylene oxide or mixture thereof. In one specific embodiment, the organic chemical stream comprises at least one of isobutane, propylene, propylene oxide, or a mixture thereof. Oxygenate impurities which may be removed from an organic chemical stream by the method of the present invention comprise at least one of an aldehyde, ester, carboxylic acid, or a mixture thereof. In one specific embodiment, the oxygenate impurities comprise at least one of formaldehyde, acetaldehyde, propionaldehyde, methyl formate or a mixture thereof. In such specific embodiments the reducing agent comprises sodium bisulfite and the base comprises sodium hydroxide.

In one embodiment of the disclosed invention, at least a portion of a first aqueous phase is recycled by reintroducing the portion of the first aqueous phase into an organic chemical stream coincident with the introduction of the aqueous reducing agent into the organic chemical stream. In another embodiment, at least a portion of a second aqueous phase is recycled by reintroducing the portion of the second aqueous phase into the first purified organic chemical stream coincident with the introduction of the aqueous base into the first purified organic chemical stream.

In one aspect of the disclosed invention, an aqueous reducing agent is introduced in a molar equivalent excess relative to the level of oxygenate impurities present. In another aspect, the aqueous base is also introduced in a molar equivalent excess relative to the level of oxygenate impurities present.

In certain aspects of the present invention, mixing of an organic chemical stream with an aqueous reducing agent occurs in a static mixer. Similarly, in other aspects of the present invention, mixing of a first purified organic chemical stream with an aqueous base occurs in a static mixer. In one specific embodiment of the invention, separating of an organic chemical phase from an aqueous reducing agent phase occurs in a coalescer. In another specific embodiment of the invention, separating of a first purified organic chemical phase from an aqueous base phase occurs in a coalescer. In certain other specific embodiments, a pressure is maintained between about 65 pounds per square inch absolute (psia) and about 450 psia, and a temperature is maintained between about −50 degrees Fahrenheit (° F.) and about 150° F.

In one embodiment, the disclosed invention is a method for purifying a propylene stream containing oxygenate impurities comprising one or more aldehydes and one or more esters. Aqueous sodium bisulfite is introduced into a propylene stream and the aqueous sodium bisulfite and the propylene stream are mixed such that a first emulsion is formed, and such that the aqueous sodium bisulfite reacts with the aldehydes to form one or more aqueous phase reduction products or aqueous phase first reaction products. The first emulsion is introduced into a first coalescer and the first emulsion is separated into a first propylene layer and a first aqueous layer comprising one or more aqueous phase reduction products within the first coalescer. At least a portion of the first aqueous layer is recycled by reintroducing the portion of the first aqueous layer into the propylene stream coincident with the introduction of the aqueous sodium bisulfite into the propylene stream. The first propylene layer is removed from the first coalescer, such that the first propylene layer comprises a first purified propylene stream. The aqueous sodium hydroxide is introduced into a first purified propylene stream and the aqueous sodium hydroxide and the first purified propylene stream are mixed such that a second emulsion is formed and the aqueous sodium hydroxide reacts with the esters to form one or more aqueous phase second reaction products. The method also includes introducing the second emulsion into a second coalescer and separating the second emulsion into a second propylene layer and a second aqueous layer comprising the one or more aqueous phase hydrolysis products within the second coalescer. The method may also include recycling at least a portion of the second aqueous layer by reintroducing the portion of the second aqueous layer into the first purified propylene stream coincident with the introduction of the aqueous sodium hydroxide into the first purified propylene stream, and removing the second propylene layer from the second coalescer, such that the second propylene layer comprises a second purified propylene stream. In one embodiment, the aldehydes may include at least one of formaldehyde, acetaldehyde, propionaldehyde, butyraldhyde, isobutyraldehyde or a mixture thereof, and the esters may comprise at least one of methyl formate, ethyl formate, propyl formate, butyl formate, isobutyl formate, methyl acetate, ethyl acetate, propyl acetate, butyl acetate, isobutyl acetate or a mixture thereof. In one embodiment, the propylene stream may flow from a propylene recovery column, and the second purified propylene stream may flow to a propylene recycle column. The method may further include steps wherein mixing occurs in a static mixer. In certain specific aspects of the invention, a first coalescer comprises a drum separator and a coalescing pad, and the second coalescer comprises a sand filter. In other aspects, the propylene stream comprises about 5% to about 15% propane by weight. In another aspect, aqueous sodium bisulfite is introduced at between about 5% and about 15% molar equivalent excess relative to the level of aldehyde impurities present. In specific embodiments of the invention, aqueous sodium hydroxide is introduced at between about 5% and about 15% molar equivalent excess relative to the level of ester impurities present. In other specific embodiments, a pressure is maintained between about 250 psia and about 350 psia, and a temperature is maintained between about 10° F. and about 35° F.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1:
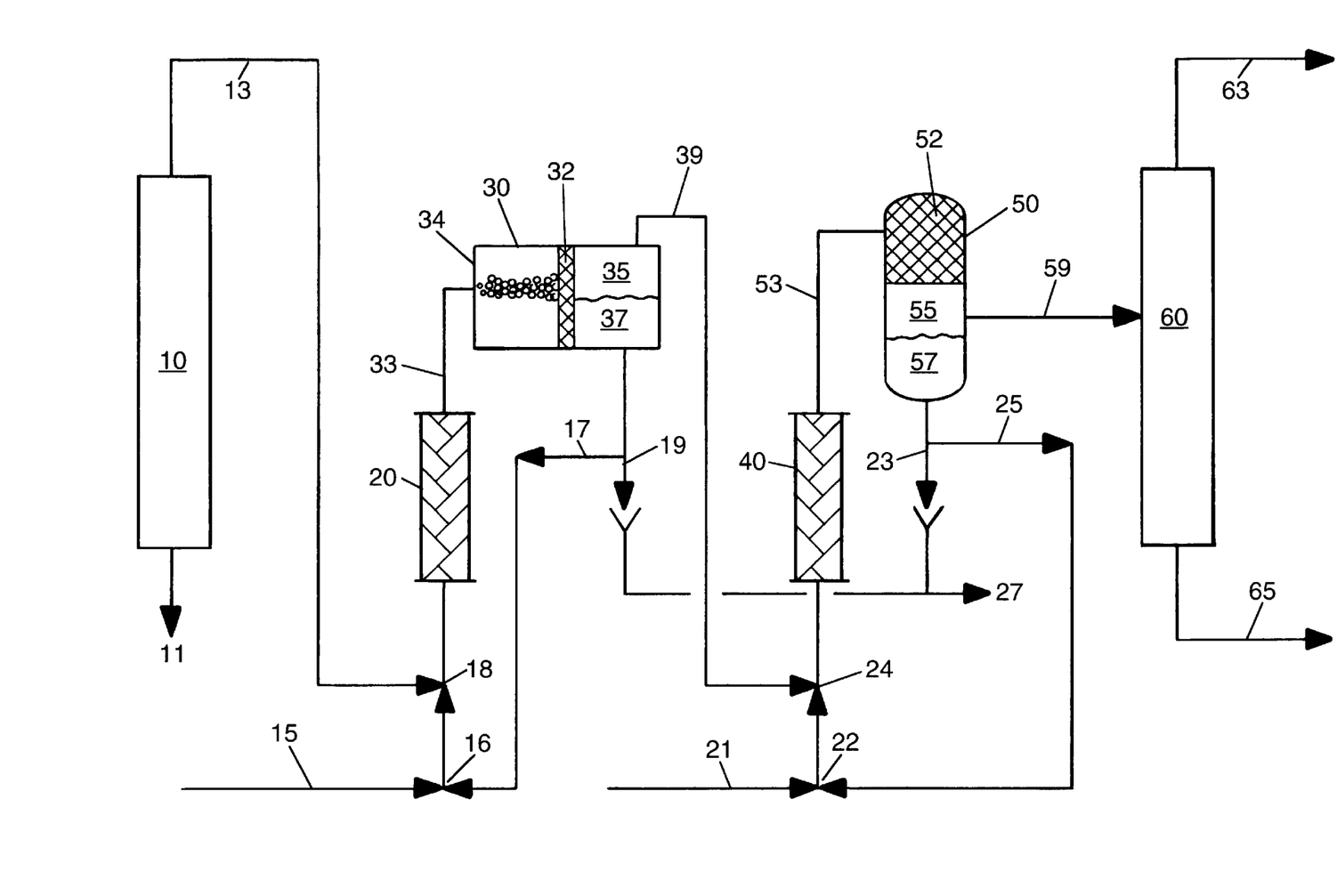
The FIGURE is a schematic drawing detailing the steps entailed in the removal of oxygenate impurities from a propylene feed, according to one embodiment of the disclosed method.

As discussed hereinabove, during the commercial manufacture of alkylene oxides, oxygenate impurities such as aldehydes and esters are produced. Such oxygenate impurities may be very difficult to separate from the alkylene oxide product, due to small differences in boiling points and other physical properties between the product and the impurities.

Disclosed herein is a method for removing oxygenate impurities from an organic chemical feed or stream (as used herein, an "organic chemical" is one comprising carbon). In one embodiment, removal is accomplished by means of introducing an aqueous solution of reducing agent and/or an aqueous solution of base into the organic chemical stream, whereby the aqueous reducing agent and base may react with oxygenate impurities present to form respective aqueous reaction products. Advantageously, the disclosed method may be used to remove both aldehyde and ester impurities, as well as other oxygenate impurities in the organic chemical stream. For example, a reducing agent may react with, among other things, aldehyde impurities to form an aldehyde-reducing agent complex, and the base may react with, among other things, ester impurities to hydrolyze them. The reaction products are typically water soluble and, by virtue of this fact, may be removed from organic chemical streams via any suitable means of separation. In a typical embodiment of the disclosed method, aqueous waste or washings containing reducing agent and its related reaction product (such as aldehyde-reducing agent complex) may be pH neutral or slightly acidic, and aqueous waste or washings containing base and its related reaction product (such as ester hydrolysis products) may be alkaline. Surprisingly, the two aqueous washings may be combined such that any excess reducing agent exerts a buffering effect upon any excess base, rendering the combined aqueous washings suitable for conventional waste water disposal.

Organic chemical streams or feeds which may be treated by means of the disclosed method may include, but are not limited to, hydrocarbons such as alkanes, alkenes, alkynes, and mixtures and/or derivatives thereof. Specific examples of suitable organic chemical streams include, but are not limited to, ethane, propane, butane, isobutane, pentanes, ethene or ethylene, propene or propylene, 1-butene or 1-butylene, 2-butene or 2-butylene, ethyne, propyne, 1-butyne, 2-butyne, ethylbenzene, and propylbenzene, as well as mixtures and/or derivatives thereof. In one typical embodiment, an organic chemical stream treatable by the disclosed method includes epoxides, and mixtures thereof and is more typically at least one of ethylene oxide, propylene oxide, butylene oxides, or a mixture thereof.

In one embodiment of the disclosed method for removal of oxygenate impurities from organic chemical streams, the organic chemical streams being treated may be drawn, for example, from any of several locations in an alkylene oxide processing facility. For example, in a typical facility designed to produce propylene oxide, there are at least three possible sources from which to draw an organic chemical stream for treatment with the disclosed method. For example, isobutane from the isobutane recycle column, propylene from the propylene recovery column, and propylene oxide from the impurities removal column are all possible streams or feeds which may be treated by means of the disclosed method.

In the practice of the disclosed method, an oxygenate impurity may be any impurity which may be removed from an organic chemical stream by means of a reducing agent and/or base such as disclosed herein. Examples of suitable types of oxygenate impurities which may be removed from organic chemical feeds or streams by means of the disclosed method include, but are not limited to, aldehydes, esters, carboxylic acids, and mixtures and/or derivatives thereof. For example, oxygenate impurities which may be removed from organic chemical feeds or streams by means of the disclosed method include, but are not limited to, aldehydes such as formaldehyde, acetaldehyde, propionaldehyde, butyraldehyde and isobutyraldehyde. Other examples of oxygenate impurities which may be removed from organic chemical feeds or streams by means of the disclosed method include, but are limited to, esters such as methyl formate, ethyl formate, propyl formate, butyl formate, isobutyl formate, methyl acetate, ethyl acetate, propyl acetate, butyl acetate and isobutyl acetate. Additional examples of oxygenate impurities which may be removed from organic chemical feeds or streams by means of the disclosed method include, but are not limited to, carboxylic acids such as formic acid, acetic acid, propionic acid, butyric acid and isobutyric acid.

It will be understood with benefit of the present disclosure that impurities other than oxygenates may optionally be present in organic chemical streams treated by means of the disclosed method. For example, alkanes may be present in alkylene streams being treated and, in one embodiment, a propylene stream may contain between about 1% to about 25% propane by weight, depending upon the point in the propylene oxide production process accessed for treatment. Advantageously, the presence of these or other similar impurities have no deleterious effect on the practice of the disclosed method.

In one embodiment of the disclosed method for removal of oxygenate impurities from organic chemical feeds or streams, an aqueous reducing agent may be introduced into the organic chemical stream. Such a reducing agent typically reacts with, among other things, reducible oxygenate impurities, such as aldehydes, to form, for example, oxygenate-reducing agent complexes which are water soluble. In one most typical embodiment of the disclosed method, aldehyde impurities may be treated with aqueous reducing agent to form one or more aldehyde-reducing agent complexes which are water soluble, comprising one or more aqueous phase first reaction products. Reducing agents useful in the practice of the disclosed method include any reducing agent suitable for forming a reaction product with oxygenate impurities (such as an aldehyde-reducing agent reaction product) which is either water soluble or a solid precipitate. Specific examples of suitable reducing agents include, but are not limited to, sulfurous acid, sodium hydrogen sulfite, sodium sulfite, sodium metabisulfite, sodium borohydride, and potassium borohydride, as well as any suitable combinations or mixtures thereof.

In one embodiment of the disclosed method for removal of oxygenate impurities from organic chemical feeds or streams, an aqueous base may be introduced into the organic chemical stream. Such a base typically reacts with, among other things, hydrolyzable oxygenate impurities such as esters or carboxylic acids to form, for example, oxygenate-base hydrolysis products which are water soluble. In one most typical embodiment of the disclosed method, ester impurities may be treated with aqueous base to form one or more ester-base hydrolysis products which are water soluble, comprising one or more aqueous phase second reaction products. Bases useful in the practice of the disclosed method include any base suitable for forming a base-ester reaction product which is either water soluble or a solid precipitate. Specific examples include, but are not limited to, Group IA metal hydroxides such as lithium hydroxide, sodium hydroxide, potassium hydroxide, and cesium hydroxide, and Group IIA metal hydroxides such as magnesium hydroxide, calcium hydroxide, and barium hydroxide, as well as any suitable combinations thereof.

Although typical embodiments of reaction products produced by reducing agent and base with oxygenate impurities are described above, it will be understood with benefit of this disclosure that a first or second reaction product may be produced by any suitable mechanism in which oxygenate impurities are converted to water soluble or precipitate reaction products. For example, carboxylic acid impurities may be treated with aqueous base to form one or more ester-base neutralization or hydrolysis products which are water soluble, comprising one or more aqueous phase second reaction products.

In a most typical embodiment of the disclosed method, both aqueous reducing agent and aqueous base are introduced into an organic chemical stream continuing both reducible and hydrolyzable oxygenate impurities to be treated, typically in sequential fashion, with the aqueous reducing agent introduced first and the aqueous base introduced second. However, it will be understood with benefit of the present disclosure that the order of may be reversed, with the aqueous base introduced first and the aqueous reducing agent introduced second, without compromising the efficacy of the disclosed method. It will also be understood that neither reducible and/or hydrolizable impurities need necessarily be present to obtain benefit of the disclosed method.

Any concentrations of aqueous reducing agent and aqueous base suitable for practicing the disclosed method may be employed. Typically, viscosity or resistance to flow of such solutions increases as they approach their saturation point, and this may optionally be a consideration in choosing concentrations of reducing agent and base for use in the disclosed method. In one embodiment employing sodium bisulfite reducing agent and sodium hydroxide base to remove oxygenate impurities from an alkylene stream such as a propylene stream, an aqueous sodium bisulfite solution typically comprises between about 0.1% and about saturation level (about 60%), more typically between about 5% and about 40%, and most typically between about 10% and about 20% sodium bisulfite by weight, and an aqueous sodium hydroxide solution typically comprises between about 0.1% and about saturation level (about 50%), more typically between about 10% and about 40%, and most typically between about 12% and about 22% sodium hydroxide by weight. These percentages are approximate and it will be understood with benefit of this disclosure that an aqueous sodium bisulfite solution may also comprise less than 0.1% or more than 60% by weight sodium bisulfite, and an aqueous sodium hydroxide solution may also comprise less than 0.1% or more than 50% by weight sodium hydroxide. Furthermore, percent compositions of sodium bisulfite and sodium hydroxide may be varied independently and substantially in the practice of the disclosed method.

As previously mentioned, aqueous reducing agent and/or aqueous base are typically introduced at separate points into an organic chemical stream to form respective emulsions. In this regard, an optional mixer or mixing device is typically located downstream of each introduction point, although such a mixing device may also be located concurrent with the introduction point, as well. In a most typical embodiment of the disclosed method, static mixers are employed which may contain fixed blades disposed at angles relative to one another, such that swirling or turbulence is induced in a feed or stream passing through the static mixer. This swirling or turbulence may promote mixing and may bring about increased contact between the components of a mixture. However, with benefit of this disclosure, it will be readily apparent that any other known means suitable for mixing an organic chemical phase and an aqueous phase, such that increased contact is achieved between the components of the mixture, may optionally be employed in the practice of the disclosed method. Such mixing means include, but are not limited to, mixing devices having mechanical, non-mechanical, or sonic mixing means. Furthermore, it will be understood with benefit of the present disclosure that mixing of an organic chemical stream and any aqueous reducing agent or base introduced therein may optionally be achieved without the presence of a mixer or mixing device.

In the practice of the disclosed method, an emulsion comprising an organic phase (organic chemical stream) and an accompanying aqueous phase (reducing agent, base, and/or related reaction products), may be separated into its constituents using any suitable separation method, including any suitable separator or separation device. Suitable separation devices include, but are not limited to, settling tanks, cyclone separators and coalescers. Known cyclone separators may be conically shaped, rapidly rotating devices which make use of centrifugal force to separate matter on the basis of mass. Typically, separations are carried out within coalescers by contacting the emulsions of the method to a coalescing means. As used herein, a "coalescer" is any containment vessel having a coalescing means disposed within. Such "coalescers" may include a coalescing pad; a sand filter comprising sand particles, other suitably small and inert particles or any other suitable porous, high surface area material which promotes coalescing of immiscible liquid phases. Preferential coalescence of the aqueous phase may occur on the coalescing means by virtue of the fact that the relatively polar aqueous phase possesses a higher surface tension than the relatively non-polar hydrocarbon phase. Typically, a first coalescer for separating an organic chemical phase from an aqueous phase comprising one or more aqueous phase first reaction products comprises at least a drum separator and a coalescing pad. Typically, a second coalescer for separating an organic chemical phase from an aqueous phase comprising one or more aqueous phase second reaction products comprises at least a sand filter. In this regard, it has been found that sand functions as an effective coalescing means in separating emulsions comprising caustic. However, other suitable separation devices may be employed in either case.

In one typical embodiment of the disclosed method, aqueous sodium bisulfite reducing agent and/or aqueous sodium hydroxide base or caustic are introduced into an organic chemical stream at about a 10% molar equivalent excess relative to the level of corresponding oxygenate impurities present. In this regard, a 10% molar equivalent excess is an approximate figure and it will be appreciated with benefit of the present disclosure that amounts of reducing agent and base may be independently varied substantially, as necessary, without exceeding the scope of the disclosed method. Typically, between about 1% and about 200%, more typically between about 2% and about 50%, and most typically between about 5% and about 15%, molar equivalent excess of reducing agent (typically relative to aldehyde levels) may be employed in the practice of the disclosed method. Likewise, typically between about 1% and about 200%, more typically between about 2% and about 50%, and most typically between about 5% and about 15%, molar equivalent excess of base (typically relative to ester and/or carboxylic acid levels) may be employed in the practice of the disclosed method. Furthermore, it will be appreciated with benefit of the present disclosure that any amount, including stoichiometric and substoichiometric amounts, of reducing agent and/or base suitable for removing oxygenate impurities from an organic chemical stream may be employed. Typically, a molar equivalent excess of reducing agent and a molar equivalent excess of base are employed; however, this need not always be the case. Furthermore, the amount of molar equivalent excess of reducing agent and the amount of molar equivalent excess of base which are employed need not be identical.

In the practice of the disclosed method, the amounts of oxygenate impurities may be any level suitable for treating with reducing agent or base to remove at least a portion of the impurities. However, levels of oxygenate impurities in an organic chemical stream typically range from about 1% (10,000 ppm) or more to as low as about 1 ppm or less. In one embodiment in which an organic recycle stream is treated or purified, oxygenate impurities may initially comprise as much as about 0.2% (2000 ppm) of the total organic chemical stream to be treated, and the levels of oxygenate impurities may typically decrease to levels of about 400 ppm or less as steady-state conditions are approached during treatment. It will be appreciated that amounts of oxygenates greater than 1% and less than 0.2% are also possible.

The disclosed method for removal of oxygenate impurities from an organic chemical stream is suitable for use over a wide range of operating conditions. This includes any range of temperatures or pressures in which the reactions necessary for practicing the disclosed method may occur. For example, in one embodiment the disclosed method may be employed in an alkylene oxide plant in which pressure is typically maintained in a range between about 65 pounds per square inch absolute (psia) and about 450 psia, more typically between about 150 psia and about 400 psia, and most typically between about 280 psia and about 320 psia. Depending upon the point in the alkylene oxide process accessed for treatment, and depending upon variables such as the temperature of cooling water, the presence of refrigeration, and the operating pressures employed, temperatures in a typical alkylene oxide plant in which the disclosed method is practiced are typically maintained in a range between about −50 degrees Fahrenheit (° F.) and about 150° F., more typically between about 10° F. and about 110° F., and most typically between about 10° F. and about 35° F. Typically, sufficiently low temperatures may serve to freeze the aqueous phase, causing it to solidify, thereby having a deleterious effect on the practice of the disclosed method, and this may be a consideration in choosing operating temperatures for practice of the disclosed method. It will be understood with benefit of this disclosure that the disclosed method may also be practiced at temperatures greater than about 150° F. and less than about −50° F., and/or at pressures greater than about 450 psia and less than about 65 psia.

The FIGURE shows a schematic diagram for one typical embodiment of the disclosed method as practiced in a propylene oxide production facility. However, it will be understood with benefit of the present disclosure that the disclosed method may be practiced in plants, facilities, or processes other than an alkylene oxide production facility. In this regard, columns 10 and 60 of The FIGURE may not be present. As shown, a stream 11 of crude propylene oxide flows from the bottom of propylene recovery column 10, and a stream 13 of propylene, which may contain oxygenate impurities, flows from the top of propylene recovery column 10. Aqueous sodium bisulfite 15 is introduced into propylene stream 13 at introduction point 18, and the propylene stream and aqueous sodium bisulfite are mixed by passing through static mixer 20. Static mixer 20 may contain fixed blades disposed at angles relative to one another, such that swirling or turbulence is induced in the propylene stream and accompanying aqueous sodium bisulfite passing through static mixer 20. The swirling or turbulence in the flow of the propylene stream and accompanying aqueous sodium bisulfite results in the formation of a first emulsion 33 comprising a propylene phase and an aqueous phase. Formation of this first emulsion allows greater contact between the sodium bisulfite reducing agent in the aqueous phase and the oxygenate impurities in the propylene phase. In this regard, the sodium bisulfite reducing agent and oxygenate impurities (typically aldehydes) typically react to form water soluble aldehyde-bisulfite complexes, or aqueous phase first reaction products.

Next, first emulsion 33 is typically introduced into first coalescer 30, which typically consists of drum separator 34 containing porous coalescing pad 32. As first emulsion 33 flows through porous coalescing pad 32, droplets of the aqueous phase condense upon the surfaces of coalescing pad 32, resulting in separation of the propylene phase and the aqueous phase. Preferential condensation of the aqueous phase may occur on the coalescing pad 32 by virtue of the fact that the relatively polar aqueous phase possesses a higher surface tension than the relatively non-polar propylene phase. Typically, first emulsion 33 within first coalescer 30 is separated into first propylene layer 35 and first aqueous layer 37, with denser aqueous layer 37 on the bottom. First aqueous layer 37, which contains water soluble aldehyde-bisulfite complex reaction products, may be drawn off and discarded or sent to waste water treatment 27 at this juncture. Typically, however, only a relatively small first portion 19 of first aqueous layer 37 is discarded, with the remaining second portion 17 of first aqueous layer 37 being recycled by reintroducing it into the propylene stream at a point 16 near or coincident with the point at which aqueous sodium bisulfite 15 is introduced into propylene stream 13. Advantageously, this recycling of the majority of first aqueous layer 37 may ensure that unreacted sodium bisulfite reducing agent is again mixed with propylene stream 13 containing oxygenate impurities, thereby bolstering the overall efficiency of the oxygenate removal process.

First propylene layer 35, upon removal from first coalescer 30, comprises a first purified propylene stream 39 which may have a reduced concentration of oxygenate impurities. In this regard, a "purified propylene stream" is used herein to mean a propylene stream which has had at least a portion of one or more oxygenate impurities contained therein at least partially decomposed or removed. Aqueous sodium hydroxide 21 is introduced at point 24 into first purified propylene stream 39 flowing from first coalescer 30, and first purified propylene stream 39 and accompanying aqueous sodium hydroxide are mixed by passing through static mixer 40. Static mixer 40 may contain fixed blades disposed at angles relative to one another, such that swirling or turbulence is induced in first purified propylene stream 39 and accompanying aqueous sodium hydroxide passing through static mixer 40. The swirling or turbulence in the flow of the first purified propylene stream and the accompanying aqueous phase results in the formation of a second emulsion 53 comprising a first purified propylene phase and an aqueous phase. Formation of this second emulsion allows greater contact between the sodium hydroxide base in the aqueous phase and the oxygenate impurities in the propylene phase. In this regard, the sodium hydroxide base and oxygenate impurities (typically esters such as methyl formate) typically react to form water soluble hydrolysis products, or aqueous phase second reaction products.

Next, second emulsion 53 is typically introduced into second coalescer 50 which typically includes a porous sand filter 52. As second emulsion 53 flows through porous sand filter 52, droplets of the aqueous phase condense upon the surfaces of the sand particles, resulting in separation of the propylene phase and aqueous phase. Preferential condensation of the aqueous phase may occur on the sand filter 52 by virtue of the fact that the relatively polar aqueous phase possesses a higher surface tension than the relatively nonpolar propylene phase. Typically, the second emulsion within second coalescer 50 is separated into second propylene layer 55 and second aqueous layer 57, with the denser aqueous layer 57 settling on the bottom. Second aqueous layer 57, which contains the water soluble base hydrolysis reaction products, may be drawn off and discarded or sent to waste water treatment 27 at this juncture. Typically, however, only a relatively small first portion 23 of second aqueous layer 57 is discarded, with remaining second portion 25 of second aqueous layer 57 being recycled by reintroducing it into first purified propylene stream 39 at a point 22 near or coincident with the point at which aqueous sodium hydroxide 21 is introduced into first purified propylene stream 39. Advantageously, this recycling of the majority of second aqueous layer 57 may ensure that unreacted sodium hydroxide base is again mixed with first purified propylene stream 39 containing oxygenate impurities, thereby bolstering the overall efficiency of the oxygenate removal process. Second propylene layer 55, upon removal from second coalescer 50, comprises a second purified propylene stream 59 which may have a reduced concentration of oxygenate impurities. Second purified propylene stream 59 flows into propylene recycle column 60. Recycle propylene stream 63 flows from the top of propylene recycle column 60, and propane stream 65 flows from the bottom of propylene recycle column 60.

As mentioned above, a first portion 19 of first aqueous layer 37 present in first coalescer 30 is typically discarded, while a second portion 17 of first aqueous layer 37 in first coalescer 30 is recycled. Typically, the amount of first portion 19 of first aqueous layer 37 which is discarded comprises about 5% by volume of a total volume of first aqueous layer 37 present in first coalescer 30, with the remaining about 95% being recycled. However, with benefit of this disclosure, it will be appreciated that the ratio of discarded to recycled aqueous phase may be varied substantially and as necessary without exceeding the scope of the disclosed method. For example, the amount of first portion 19 of a total volume of first aqueous layer 37 which is actually discarded may comprise between about 0% to about 100% and include all values therebetween. Conversely, the amount of first portion 19 of a total volume of first aqueous layer 37 which is recycled may comprise between about 100% to about 0% and include all values therebetween. Similarly, a first portion 23 of second aqueous layer 57 present in second coalescer 50 is typically discarded, while a second portion 25 of second aqueous layer 57 in second coalescer 50 is recycled. Typically, the amount of first portion 23 of second aqueous layer 57 which is actually discarded comprises about 1–2% by volume of a total volume of second aqueous layer 57 present in second coalescer 50, with the remaining about 98–99% being recycled. However, with benefit of this disclosure, it will be appreciated that the ratio of discarded to recycled aqueous phase may be varied substantially and as necessary without exceeding the scope of the disclosed method. For example, the amount of first portion 23 of a total volume of second aqueous layer 57 which is actually discarded may comprise between about 0% to about 100% and include all values therebetween. Conversely, the amount of first portion 23 of a total volume of second aqueous layer 57 which is recycled may comprise between about 100% to about 0% and include all values therebetween.

It will be understood with benefit of the present disclosure that the embodiment of The FIGURE is illustrative only, and that method steps and apparatus used therein may be moved, removed, interchanged, or supplemented without departing from the scope of the disclosed method. Furthermore, in practicing the disclosed method for removal of oxygenate impurities from organic chemical feeds or streams, an organic chemical feed or stream may be treated with an aqueous reducing agent processing step, followed by treatment with an aqueous base processing step. The aqueous reducing agent processing step typically comprises introduction of an aqueous reducing agent mto the organic chemical feed or stream, mixing of the aqueous reducing agent and organic chemical feed or stream such that an emulsion is formed and a reaction occurs between the reducing agent and oxygenate impurities in the feed or stream, separation of the emulsion into an organic phase and an aqueous phase containing reaction products in a coalescer or other separator vessel, recycling of a portion of the aqueous phase, and removal of the organic phase from the closer or other separator vessel. The aqueous base processing step typically comprises introduction of an aqueous base into the organic chemical feed or stream, mixing of the aqueous base and organic chemical feed or stream such that an emulsion is formed and a reaction occurs between the base and oxygenate impurities in the feed or stream, separation of the emulsion into an organic phase and an aqueous phase containing reaction products in a coalescer or other separator vessel, recycling of a portion of the aqueous phase, and removal of the organic phase from the closer or other separator vessel. In one embodiment of the disclosed method, an organic chemical feed or stream may be treated with an aqueous base processing step, followed by treatment with an aqueous reducing agent processing step. In another embodiment of the disclosed method, an organic chemical feed or stream may be treated with an aqueous base processing step only. In yet another embodiment of the disclosed method, an organic chemical feed or stream may be treated with an aqueous reducing agent processing step only. In embodiments of the disclosed method which employ both an aqueous reducing agent processing step and an aqueous base processing step, in any sequence of steps, it is often desirable to prevent co-mingling of aqueous reducing agent and aqueous base, especially in cases where, for example, the aqueous reducing agent and aqueous base may react with one another such as in an exothermic reaction which may generate heat and impair efficacy of the disclosed method.

The following examples are included to demonstrate typical embodiments of the disclosed method. It should be appreciated by those of skill in the art that the techniques disclosed in the examples which follow represent techniques discovered by the inventor to function well in the practice of the disclosed method, and thus can be considered to constitute typical modes for its practice. However, those of skill in the art should, in light of the present disclosure, appreciate that many changes can be made in the specific embodiments which are disclosed and still obtain a like or similar result without departing from the spirit and scope of the disclosed method.

EXAMPLE 1

This example employs a stream made up of cyclohexane with small amounts of formaldehyde and methyl formate. This stream simulates a propylene stream flowing from a propylene recovery column, comprising propylene with about 12% propane, as well as the oxygenate impurities. Cyclohexane was substituted for the propylene stream in order to provide a liquid laboratory scale stream which may be contained or confined in standard laboratory glassware at ambient conditions. Acetaldehyde and methyl formate were each found to have similar partitioning coefficients in the cyclohexane/aqueous reactants laboratory scale stream relative to those observed in a typical propylene/aqueous reactants stream.

A solution of cyclohexane with 1000 ppm acetaldehyde and 500 ppm methyl formate impurities was prepared and a partitioning run was carried out in a 500 mL separatory funnel, reacting this mixture with aqueous sodium bisulfite as the reducing agent and aqueous sodium hydroxide as the base. The cyclohexane-aldehyde solution was prepared by mixing 1000 g cyclohexane, 1.0 g acetaldehyde, and 0.5 g methyl formate in a large flask. After mixing, a portion was decanted into a labeled vial for analysis. Sodium bisulfite solution was prepared by mixing 9.66 g water and 2.16 g $Na_2S_2O_5$ in a flask with shaking until complete dissolution had occurred. Sodium hydroxide solution was drawn from 0.2 N sodium hydroxide laboratory stock solution.

Into a 500 mL separatory funnel were added 1.2 grams of the sodium bisulfite solution and 100 grams of the cyclohexane-aldehyde solution. The stopper was attached and the funnel was shaken for one minute. The mixture was allowed to settle, and the lower portion was decanted. Then the calculated amount of sodium hydroxide solution was added. The stopper was attached and the funnel shaken for one minute. The mixture was allowed to settle and the lower portion was decanted. Finally, the upper organic phase was decanted into a labeled vial for analysis.

Prior to extraction, an aliquot of the cyclohexane phase was analyzed using gas chromatography (GC). Analysis results indicated an acetaldehyde concentration of about 932 ppm and a methyl formate concentration of about 528 ppm. Following extraction as described above with aqueous sodium bisulfite and aqueous sodium hydroxide, an aliquot of the cyclohexane phase was analyzed using GC analysis. Analysis results indicated an acetaldehyde concentration of about 40 ppm and a methyl formate concentration of about 42 ppm. In this partitioning run, extraction of the cyclohexane phase with aqueous sodium bisulfite and aqueous sodium hydroxide thus resulted in at least a one order of magnitude decrease of oxygenate impurities levels.

EXAMPLE 2

This example illustrates one possible application of the disclosed method employed in a propylene oxide plant. In this example, propylene is flowing at a rate of about 20,000 pounds per hour and formaldehyde and methyl formate are known to be present at levels of about 1300 parts per million (ppm) and about 700 ppm, respectively. Based on this information, it may be calculated that about 394 moles per hour of formaldehyde and about 106 moles per hour of methyl formate are flowing in the propylene stream. In such a case, about 434 moles per hour of sodium bisulfite (10% molar equivalent excess) and about 117 moles (10% molar equivalent excess) per hour of sodium hydroxide would typically be introduced into the propylene stream to reduce the level of oxygenate impurities.

While the invention may be adaptable to various modifications and alternative forms, specific embodiments have been shown by way of example and described herein However, it should be understood that the invention is not intended to be limited to the particular forms disclosed. Rather, the invention is to cover all modifications, equivalents, and alternatives falling within the spirit and scope of the invention as defined by the appended claims. Moreover, the different aspects of the disclosed methods and devices may be utilized in various combinations and/or independently. Thus the invention is not limited to only those combinations shown herein, but rather may include other combinations.

What is claimed is:

1. A method for purifying an organic chemical stream comprising oxygenate impurities, comprising:

introducing an aqueous reducing agent into said organic chemical stream under conditions such that said aqueous reducing agent reacts with a first portion of said oxygenate impurities to form one or more aqueous phase first reaction products;

removing said aqueous phase first reaction products from said organic chemical stream;

introducing an aqueous base into said organic chemical stream under conditions such that said aqueous base reacts with a second portion of said oxygenate impurities to form one or more aqueous phase second reaction products; and removing said aqueous phase second reaction products from said organic chemical stream;

wherein said first and second portions of said oxygenate impurities are present in said organic stream prior to introduction of said aqueous reducing agent and prior to introduction of said aqueous base; and wherein said aqueous reducing agent is introduced into said organic chemical stream, and said aqueous phase first reaction products removed from said organic chemical stream, prior to introduction of said aqueous base into said organic chemical stream.

2. The method of claim 1, wherein said organic chemical stream comprises at least one of an alkane, alkene, alkylene oxide or a mixture thereof and wherein said oxygenate impurities comprise at least one of an aldehyde, ester, carboxylic acid, or a mixture thereof.

3. The method of claim 2, wherein:

said alkane comprises at least one of methane, ethane, propane, butane, isobutane, or a mixture thereof;

said alkene comprises at least one of ethene, propene, 1-butene, 2-butene, or a mixture thereof;

said alkylene oxide comprises at least one of ethylene oxide, propylene oxide, butylene oxides, or a mixture thereof;

said aldehyde comprises at least one of formaldehyde, acetaldehyde, propionaldehyde, butyraldehyde, isobutyraldehyde, or a mixture thereof;

said ester comprises at least one of methyl formate, ethyl formate, propyl formate, butyl formate, isobutyl formate, methyl acetate, ethyl acetate, propyl acetate, butyl acetate, isobutyl acetate, or a mixture thereof; and said carboxylic acid comprises at least one of formic acid, acetic acid, propionic acid, butyric acid, isobutyric acid, or a mixture thereof.

4. The method of claim 1, wherein said reducing agent comprises at least one of sulfurous acid, sodium bisulfite, sodium sulfite, sodium metabisulfite, or a mixture thereof, and wherein said base comprises at least one of lithium hydroxide, sodium hydroxide, potassium hydroxide, cesium hydroxide, or a mixture thereof.

5. The method of claim 1, wherein said organic chemical stream comprises propylene and said oxygenate impurities comprise at least one of an aldehyde, ester, or a mixture thereof.

6. The method of claim 1, further comprising combining at least a portion of said aqueous phase first reaction products with at least a portion of said aqueous phase second reaction products such that any excess reducing agent present in said combination exerts a buffering effect upon any excess base present in said combination.

7. A method for purifying an organic chemical stream, said organic chemical stream comprising one or more oxygenate impurities, comprising the steps of:

introducing an aqueous base into said organic chemical stream and mixing said aqueous base and said organic chemical stream such that a first emulsion is formed and said aqueous base reacts with said oxygenate impurities to form one or more aqueous phase first reaction products;

separating said first emulsion into a first organic chemical phase and a first aqueous phase comprising said aqueous phase first reaction products; and removing said first aqueous phase from said first organic chemical phase such that said first organic chemical phase comprises a first purified organic chemical stream;

introducing an aqueous reducing agent into said first purified organic chemical stream and mixing said aqueous reducing agent and said first purified organic chemical stream such that a second emulsion is formed and said aqueous reducing agent reacts with at least a second portion of said oxygenate impurities to form one or more aqueous phase second reaction products;

separating said second emulsion into a second organic chemical phase and a second aqueous phase comprising said aqueous phase second reaction products;

removing said second aqueous phase from said second organic chemical phase such that said second organic chemical phase comprises a second purified organic chemical stream.

8. The method of claim 7, wherein said organic chemical stream comprises at least one of an alkane, alkene, alkylene oxide or a mixture thereof and wherein said oxygenate impurities comprise at least one of an aldehyde, ester, carboxylic acid, or a mixture thereof.

9. The method of claim 8, wherein:

said alkane comprises at least one of methane, ethane, propane, butane, isobutane, or a mixture thereof;

said alkene comprises at least one of ethene, propene, 1-butene, 2-butene, or a mixture thereof;

said alkylene oxide comprises at least one of ethylene oxide, propylene oxide, butylene oxides, or a mixture thereof;

said aldehyde comprises at least one of formaldehyde, acetaldehyde, propionaldehyde, butyraldehyde, isobutyraldehyde, or a mixture thereof;

said ester comprises at least one of methyl formate, ethyl formate, propyl formate, butyl formate, isobutyl formate, methyl acetate, ethyl acetate, propyl acetate, butyl acetate, isobutyl acetate, or a mixture thereof; and said carboxylic acid comprises at least one of formic acid, acetic acid, propionic acid, butyric acid, isobutyric acid, or a mixture thereof.

10. The method of claim 7, wherein said reducing agent comprises at least one of sulfurous acid, sodium bisulfite, sodium sulfite, sodium metabisulfite, or a mixture thereof, and wherein said base comprises at least one of lithium hydroxide, sodium hydroxide, potassium hydroxide, cesium hydroxide, or a mixture thereof.

11. The method of claim 7, wherein said organic chemical stream comprises propylene and said oxygenate impurities comprise at least one of an aldehyde, ester, or a mixture thereof.

12. A method for purifying an organic chemical stream, said organic chemical stream comprising one or more oxygenate impurities, comprising:

introducing an aqueous reducing agent into said organic chemical stream and mixing said aqueous reducing agent and said organic chemical stream such that a first emulsion is formed and said aqueous reducing agent reacts with at least a first portion of said oxygenate impurities to form one or more aqueous phase first reaction products;

separating said first emulsion into a first organic chemical phase and a first aqueous phase comprising said aqueous phase first reaction products;

removing said first aqueous phase from said first organic chemical phase such that said first organic chemical phase comprises a first purified organic chemical stream;

introducing an aqueous base into said first purified organic chemical stream and mixing said aqueous base and said first purified organic chemical stream such that a second emulsion is formed and said aqueous base reacts with said oxygenate impurities to form one or more aqueous phase second reaction products;

separating said second emulsion into a second organic chemical phase and a second aqueous phase comprising said aqueous phase second reaction products; and removing said second aqueous phase from said second organic chemical phase such that said second organic chemical phase comprises a second purified organic chemical stream.

13. The method of claim 12, wherein said organic chemical stream comprises at least one of an alkane, alkylene, alkylene oxide or mixture thereof; and wherein said one or more oxygenate impurities comprises at least one of an aldehyde, ester, carboxylic acid, or a mixture thereof.

14. The method of claim 12, wherein said organic chemical stream comprises at least one of isobutane, propylene, propylene oxide, or a mixture thereof; and wherein said one or more oxygenate impurities comprises at least one of an aldehyde, ester, carboxylic acid, or a mixture thereof.

15. The method of claim 12, wherein said organic chemical stream comprises propylene; wherein said oxygenate impurities comprise at least one of formaldehyde, acetaldehyde, propionaldehyde, methyl formate or a mixture thereof; wherein said reducing agent comprises sodium bisulfite; and wherein said base comprises sodium hydroxide.

16. The method of claim 12, wherein at least a portion of said first aqueous phase is recycled by reintroducing said portion of said first aqueous phase into said organic chemical stream coincident with the introduction of said aqueous reducing agent into said organic chemical stream; and wherein at least a portion of said second aqueous phase is recycled by reintroducing said portion of said second aqueous phase into said first purified organic chemical stream coincident with the introduction of said aqueous base into said first purified organic chemical stream.

17. The method of claim 12, wherein
said aqueous reducing agent is introduced in a molar equivalent excess relative to the level of oxygenate impurities present; and
said aqueous base is introduced in a molar equivalent excess relative to the level of said oxygenate impurities present.

18. The method of claim 12, wherein said mixing occurs in a static mixer.

19. The method of claim 12, wherein said separating occurs in a coalescer.

20. The method of claim 12, wherein a pressure is maintained between about 65 psia and about 450 psia, and a temperature is maintained between about −50° F. and about 150° F.

21. The method of claim 12, further comprising combining at least a portion of said aqueous phase first reaction products with at least a portion of said aqueous phase second reaction products such that any excess reducing agent present in said combination exerts a buffering effect upon any excess base present in said combination.

22. The method of claim 12, wherein said organic chemical stream comprises propane; wherein said oxygenate impurities comprise at least one of formaldehyde, acetaldehyde, propionaldehyde, methyl formate or a mixture thereof; wherein said reducing agent comprises sodium bisulfite; and wherein said base comprises sodium hydroxide.

23. The method of claim 12, wherein said organic chemical stream comprises alkene; and wherein said oxygenate impurities comprises at least one of ester, aldehyde, or a mixture thereof.

24. A method for purifying a propylene stream containing oxygenate impurities, said oxygenate impurities comprising one or more aldehydes and one or more esters, comprising:

introducing aqueous sodium bisulfite into said propylene stream and mixing said aqueous sodium bisulfite and said propylene stream such that a first emulsion is formed and said aqueous sodium bisulfite reacts with said aldehydes to form one or more aqueous phase first reaction products;

introducing said first emulsion into a first coalescer and separating said first emulsion into a first propylene layer and a first aqueous layer comprising said one or more aqueous phase reduction products within said first coalescer;

recycling at least a portion of said first aqueous layer by reintroducing said portion of said first aqueous layer into said propylene stream coincident with the introduction of said aqueous sodium bisulfite into said propylene stream;

removing said first propylene layer from said first coalescer, such that said first propylene layer comprises a first purified propylene stream;

introducing aqueous sodium hydroxide into said first purified propylene stream and mixing said aqueous sodium hydroxide and said first purified propylene stream such that a second emulsion is formed and said aqueous sodium hydroxide reacts with said esters to form one or more aqueous phase second reaction products;

introducing said second emulsion into a second coalescer and separating said second emulsion into a second propylene layer and a second aqueous layer comprising said one or more aqueous phase hydrolysis products within said second coalescer;

recycling at least a portion of said second aqueous layer by reintroducing said portion of said second aqueous layer into said first purified propylene stream coincident with the introduction of said aqueous sodium hydroxide into said first purified propylene stream; and removing said second propylene layer from said second coalescer, such that said second propylene layer comprises a second purified propylene stream.

25. The method of claim 24, wherein
said aldehydes comprise at least one of formaldehyde, acetaldehyde, propionaldehyde, butyraldhyde, isobutyraldehyde or a mixture thereof; and
said esters comprise at least one of methyl formate, ethyl formate, propyl formate, butyl formate, isobutyl formate, methyl acetate, ethyl acetate, propyl acetate, butyl acetate, isobutyl acetate or a mixture thereof.

26. The method of claim 24, wherein said propylene stream flows from a propylene recovery column, and said second purified propylene stream flows to a propylene recycle column.

27. The method of claim 24, wherein said mixing occurs in a static mixer.

28. The method of claim 24, wherein said first coalescer comprises a drum separator and a coalescing pad, and said second coalescer comprises a sand filter.

29. The method of claim 24, wherein said propylene stream comprises about 5% to about 15% propane by weight.

30. The method of claim 24, wherein said aqueous sodium bisulfite is introduced at between about 5% and about 15% molar equivalent excess relative to the level of aldehyde impurities present.

31. The method of claim 24, wherein said aqueous sodium hydroxide is introduced at between about 5% and about 15% molar equivalent excess relative to the level of ester impurities present.

32. The method of claim 24, wherein a pressure is maintained between about 250 psia and about 350 psia, and a temperature is maintained between about 10° F. and about 35° F.

33. The method of claim 24, further comprising combining at least a portion of said aqueous phase first reaction products with at least a portion of said aqueous phase second reaction products such that any excess reducing agent present in said combination exerts a buffering effect upon any excess base present in said combination.

* * * * *